(12) United States Patent
Rotem et al.

(10) Patent No.: US 9,950,151 B2
(45) Date of Patent: Apr. 24, 2018

(54) IMPLANTABLE MEDICAL DEVICES

(71) Applicant: Beta-O2 Technologies Ltd., Kiryat Aryeh (IL)

(72) Inventors: Avi Rotem, Petach-Tikva (IL); Uriel Barkai, Kibutz Nachsholim (IL); Baruch Zimerman, Modiin (IL); Zohar Gendler, Zichron Yaakov (IL)

(73) Assignee: Beta-O2 Technologies Ltd., Kiryat Aryeh (IL)

( * ) Notice: Subject to any disclaimer, the term of this patent is extended or adjusted under 35 U.S.C. 154(b) by 710 days.

(21) Appl. No.: 14/227,258

(22) Filed: Mar. 27, 2014

(65) Prior Publication Data

US 2015/0273200 A1    Oct. 1, 2015

(51) Int. Cl.
*A61M 39/02* (2006.01)
*A61M 5/142* (2006.01)

(52) U.S. Cl.
CPC .... *A61M 39/0208* (2013.01); *A61M 5/14276* (2013.01); *A61M 2005/14204* (2013.01); *A61M 2039/0211* (2013.01); *A61M 2202/0007* (2013.01); *A61M 2202/0208* (2013.01); *A61M 2202/0225* (2013.01); *A61M 2209/045* (2013.01)

(58) Field of Classification Search
CPC .......... A61M 39/0208; A61M 5/14276; A61M 2202/0007; A61M 2202/0225; A61M 2005/14204; A61M 2209/045; A61M 2202/0208; A61M 2039/0211
See application file for complete search history.

(56) References Cited

U.S. PATENT DOCUMENTS

| | | | |
|---|---|---|---|
| 2004/0133188 A1* | 7/2004 | Vardi | A61F 2/022 604/891.1 |
| 2009/0012502 A1 | 1/2009 | Rotem et al. | |
| 2010/0124564 A1* | 5/2010 | Martinson | A61K 35/39 424/424 |
| 2010/0312165 A1* | 12/2010 | Stern | C12M 21/02 604/19 |
| 2011/0054387 A1* | 3/2011 | Stern | A61M 39/0208 604/23 |

* cited by examiner

*Primary Examiner* — Nathan R Price
*Assistant Examiner* — Melissa A Snyder
(74) *Attorney, Agent, or Firm* — Greenberg Traurig, LLP

(57) ABSTRACT

An implantable medical system that comprises a gas unit for supplying gas that is essentially oxygen and at least one functional cells unit configured to receive oxygen from the gas unit so as to maintain the cells in a viable condition. The cells unit is flexible. Several embodiments are disclosed.

17 Claims, 8 Drawing Sheets

IMPLANTABLE MEDICAL DEVICES

FIELD OF THE INVENTION

The present invention relates generally to implantable medical devices having an oxygen reservoir and a flexible functional cells unit protected from the host immune system.

BACKGROUND OF THE INVENTION

Several disorders arising from hyposecretion of one or more substances such as hormones are known. Among these are diabetes, Parkinson's disease, Alzheimer's disease, hypo- and hyper-tension, hypothyroidism, and various liver disorders. The hormone insulin, for example, is produced by β-cells in the islets of Langerhans of the pancreas. In normal individuals, insulin release is regulated so as to maintain blood glucose levels in the range of about 70 to 110 milligrams per deciliter. In diabetics, insulin is either not produced at all (Type 1 diabetes), or the body cells do not properly respond to the insulin that is produced (Type 2 diabetes). The result is elevated glucose levels in the blood.

Disorders arising from hyposecretion of a hormone are usually treated by administration of the missing hormone. However, despite advances in understanding and treating many of these diseases, it is often not possible to precisely regulate metabolism with exogenous hormones. A diabetic patient, for example, is required to make several daily measurements of blood glucose levels and then inject an appropriate amount of insulin to bring the glucose levels to within the acceptable range.

Organ transplantation is not a viable treatment today for most of these disorders for several reasons including rejection of a transplanted organ by the immune system. Isolated cells may be implanted in the body after being treated to prevent rejection e.g. by immunosuppression, radiation or encapsulation. The encapsulating material is selected so as to be biocompatible and to allow diffusion of small molecules between the cells and the environment while shielding the cells from immunoglobulins and cells of the immune system. Encapsulated β-cells or islets of Langerhans (the tissue producing the insulin), for example, can be injected into the portal vein or embedded under the skin, in the abdominal cavity, or in other locations. The success of many cellular transplants is compromised not only due to graft-host rejections, but also on account of ischemic conditions generated by insufficient oxygen supply to the transplant. Following implantation of the cells, oxygen is provided to the implanted cells from the body tissue (mainly via diffusion), and in some cases, from vascular structures that form around the transplanted cells with the help of angiogenic factors, e.g., VEGF and bFGF. However, the natural diffusion rate is too low to provide the cells with a sufficient amount of oxygen, especially in macro-encapsulation and high density of the cells.

Oxygen is vital for the physiological processes and functionality of the implanted cells. An insufficient supply of oxygen to the implanted cells, often leads to cell loss of functionality or death. Oxygen provision is a vital component in sustaining transplanted cells.

Attempts are made to assure sufficient oxygen to the implanted cells. U.S. Pat. No. 7,892,222 entitled "Implantable Device"; to Vardi et al., teaches an implantable device comprising a chamber for holding functional cells and an oxygen generator for providing oxygen to the functional cells.

In one embodiment, the oxygen generator is described as comprising photosynthetic cells that convert carbon dioxide to oxygen when illuminated. In another embodiment, the oxygen generator is described as comprising electrodes that produce oxygen by electrolysis.

U.S. Pat. No. 8,012,500 to Rotem et al. describes apparatus including a chamber, which is adapted to be implanted in a body of an individual, the chamber including functional cells and chlorophyll-containing elements comprising chlorophyll of an obligate photoautotroph. Typically, the chlorophyll-containing elements include intact photosynthetic cells and/or isolated chloroplasts. The chlorophyll-containing elements provide oxygen to the functional cells and/or consume carbon dioxide produced by the functional cells.

U.S. Pat. No. 8,444,630 titled "Oxygen Supply for Cell Transplant and Vascularization" to Rotem, et al. describes an apparatus including a housing configured for insertion into a body of a patient; a photosynthetic oxygen supply configured to supply oxygen; and functional cells, coupled to the housing. The functional cells are adapted to receive the oxygen and to secrete at least one factor that induces vascularization in a vicinity of the housing when the housing is in the body of the patient. Other embodiments are also described.

When no oxygen reservoir is present, configurations of the implants is desired. An example is taught in U.S. Pat. No. 5,855,613 to Antanavich et al., entitles Retrievable Bioartificial Implants having Dimensions Allowing Rapid Diffusion of Oxygen and Rapid Biological Response to Physiological Change. This patent describes bioartificial implants and methods for their manufacture and use, particularly bioartificial pancreases. In particular, the implants may be thin sheets that enclose cells or tissue, may be completely biocompatible over extended periods of time and may induce minimal fibrosis. The viability of the high-density-cell-containing thin sheets is achieved by nourishing the tissue or cells with sufficient oxygen supply. The device is completely retrievable, and have dimensions allowing maintenance of optimal tissue viability through rapid diffusion of nutrients and oxygen and also allowing rapid secretion rate of insulin and/or other bioactive agents in response to changing physiology. Implantations of living cells, tissue, drugs, medicines and/or enzymes, contained in the bioartificial implants may be made to treat and/or prevent diseases.

SUMMARY OF THE INVENTION

The present invention relates generally to an implantable medical device having a unit that comprises the transplanted cells protected from the host immune system and oxygen unit that may be separated. One of the main objects of the embodiments described is to provide an amount of functional cells such as Islets of Langerhans that is significantly high relative to the devices that are taught in prior art documents. As an example, for effective usage of such implanted medical device, the implantation of 250,000 islets and more is needed. To minimize the volume the system occupies, high density of the islets, cells or tissues is required. In dense cells, oxygen may become the first limiting nutrient and therefore, it has to be continuously supplied at a sufficient rate. It is an object in the described embodiments to provide systems having a reservoir of gas that can assure the viability and functionality of the implanted cells, tissue or islets.

Moreover, the cell unit is thin and physically flexible in order to increase the comfort of the patient and reduce the body response to the implant expected after implantation.

It is therefore provided, in accordance with one embodiment, an implantable medical system comprising:
- a gas unit for supplying gas, wherein said gas comprises essentially oxygen;
- at least one of a plurality of functional cells unit having a certain degree of physical flexibility and configured to receive oxygen from the gas unit so as to maintain the functional cells in a viable condition.

Furthermore and in accordance with another preferred embodiment, the system further comprising at least one distributor configured to distribute the gas from said gas unit to said plurality of functional cells unit.

Furthermore and in accordance with another preferred embodiment, said gas unit is a pressurized reservoir of gas that can be replenished through a subcutaneous implantable port and wherein said port is configured to receive gas through a needle adapted to penetrate said replenishing port through skin.

Furthermore and in accordance with another preferred embodiment, a uni-directional valve is provided between the replenishing port and the pressurized reservoir to ensure gas is solely transferred from the port to the reservoir.

Furthermore and in accordance with another preferred embodiment, said gas unit is an oxygen generator.

Furthermore and in accordance with another preferred embodiment, said oxygen generator generates oxygen by hydrolysis and comprises a pair of electrodes and a power source.

Furthermore and in accordance with another preferred embodiment, the functional cells are selected from a group comprising islets of Langerhans, adrenal cells, stem cells and genetic implantable cells.

Furthermore and in accordance with another preferred embodiment, said functional cells unit has one dimension that is relatively longer than other dimensions so as to render flexibility to the unit, and wherein the unit is flexible enough so as to allow the unit to partially follow the natural movements of the body organs that are adjacent to the unit.

Furthermore and in accordance with another preferred embodiment, said functional cells unit is in a shape of a disc having a thickness of 1-8 mm and a diameter of 1-20 cm.

Furthermore and in accordance with another preferred embodiment, said functional cells unit comprises opposite positioned compartments of substantially the same dimensions, both compartments are provided with a relatively high surface area face through which oxygen can diffuse and reach the functional cells inside the unit.

Furthermore and in accordance with another preferred embodiment, the high surface area face is covered with a layer that facilitates transfer of oxygen.

Furthermore and in accordance with another preferred embodiment, said layer is a silicone layer.

Furthermore and in accordance with another preferred embodiment, outer sides of said functional cells unit is covered with another layer permeable to nutrients and bio-materials that may be produced by the functional cells and impermeable to immunologic factors and oxygen.

Furthermore and in accordance with another preferred embodiment, said compartments are disc-like and are having a thickness of about 20-2,000 µm.

Furthermore and in accordance with another preferred embodiment, the functional cells are embedded in a matrix within the unit.

Furthermore and in accordance with another preferred embodiment, said matrix is made of materials selected from a group that comprises alginate, collagen, and combination thereof.

Furthermore and in accordance with another preferred embodiment, the functional cells in the cell unit are trapped within a porous structure.

Furthermore and in accordance with another preferred embodiment, said functional cells unit comprises a plurality of subunits having substantially large surface area that allows transfer of oxygen wherein each subunit is provided with functional cells embedded in a matrix.

Furthermore and in accordance with another preferred embodiment, said subunits are arranged similarly to an egg carton, wherein the diameter of each subunit is about 10-2,500 µm.

Furthermore and in accordance with another preferred embodiment, said functional cells unit is provided with inner projections configured to allow the functional cells to be captured by.

BRIEF DESCRIPTION OF THE DRAWINGS

The invention is herein described, by way of example only, with reference to the accompanying drawings. With specific reference to the drawings in detail, it is stressed that the particulars shown are by way of example and for purposes of illustrative discussion of the preferred embodiments of the present invention only, and are presented in the cause of providing what is believed to be useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale. For clarity, non-essential elements were omitted from some of the drawings. Some optional parts were drawn using dashed lines.

Figure 1:
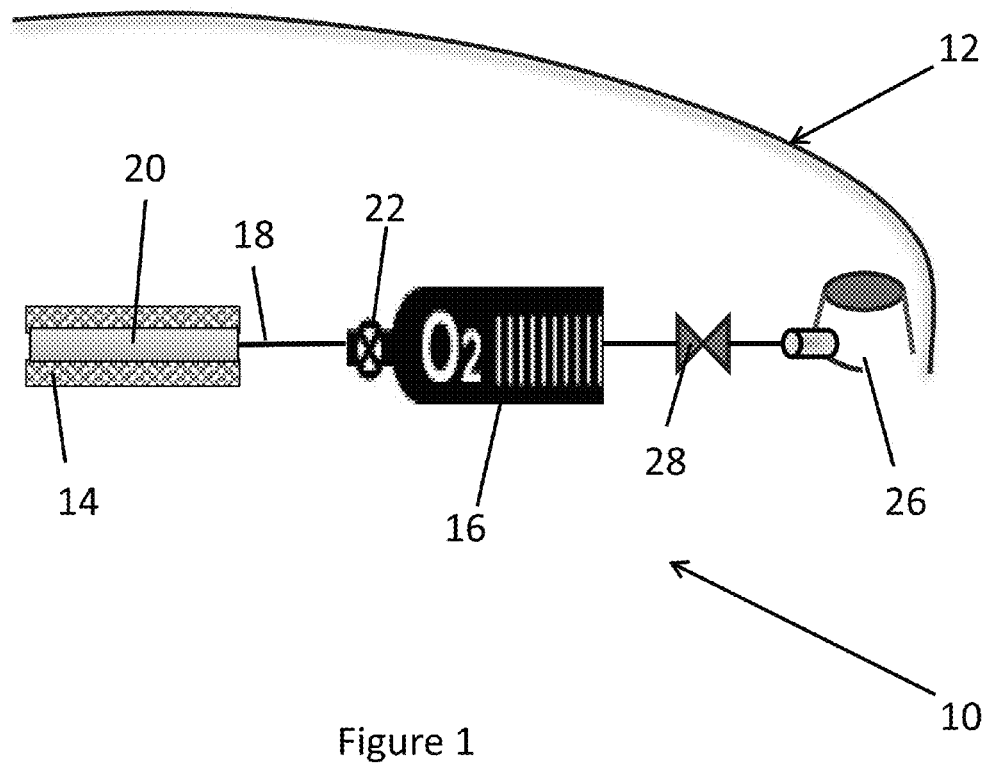

FIG. 1 schematically depicts a medical system according to an exemplary embodiment of the current invention.

Figure 2A:
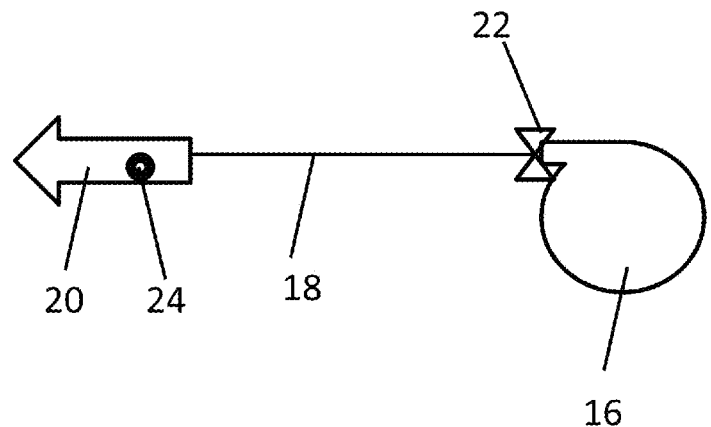

FIG. 2a illustrates a system for controlled flow of gas from the gas unit to the cells unit incorporated in the system shown in FIG. 1, in accordance with one embodiment.

Figure 2B:
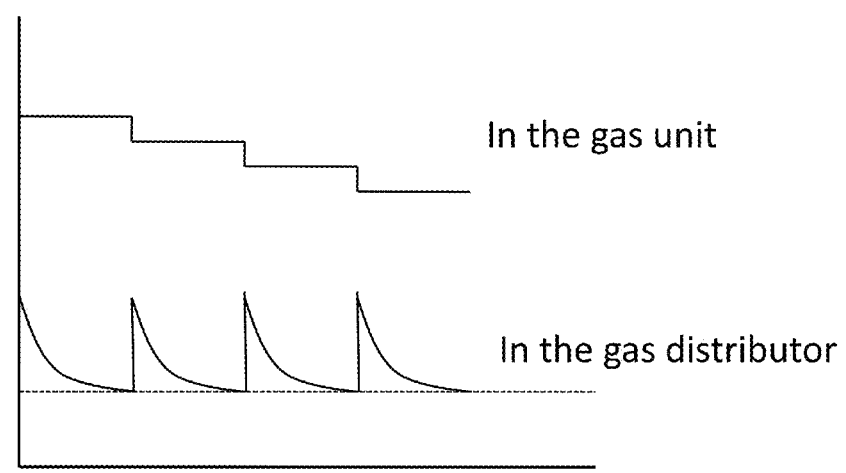

FIG. 2b schematically shows the controlled release of gas in the exemplary embodiment.

Figure 3:
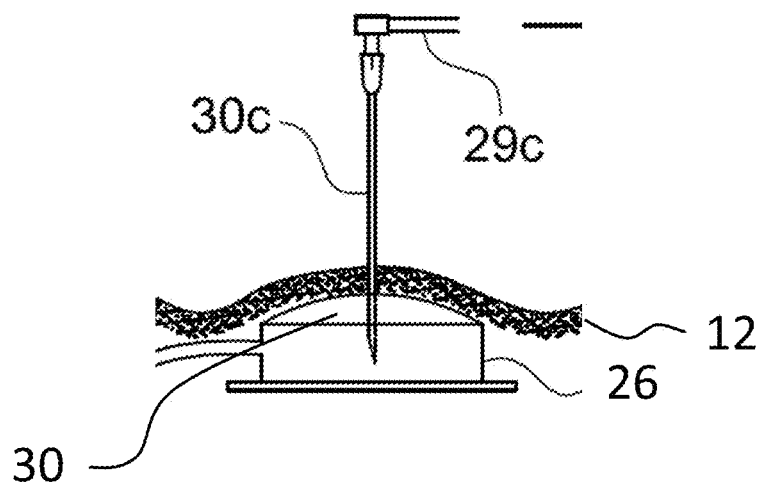

FIG. 3 illustrates the port when replenished with gas from outside the body in accordance with an exemplary embodiment.

Figure 4:
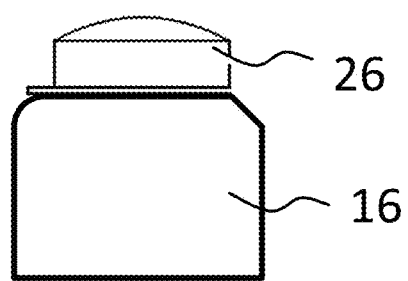

FIG. 4 illustrates a gas unit incorporated with a port in accordance with an exemplary embodiment.

Figure 5:
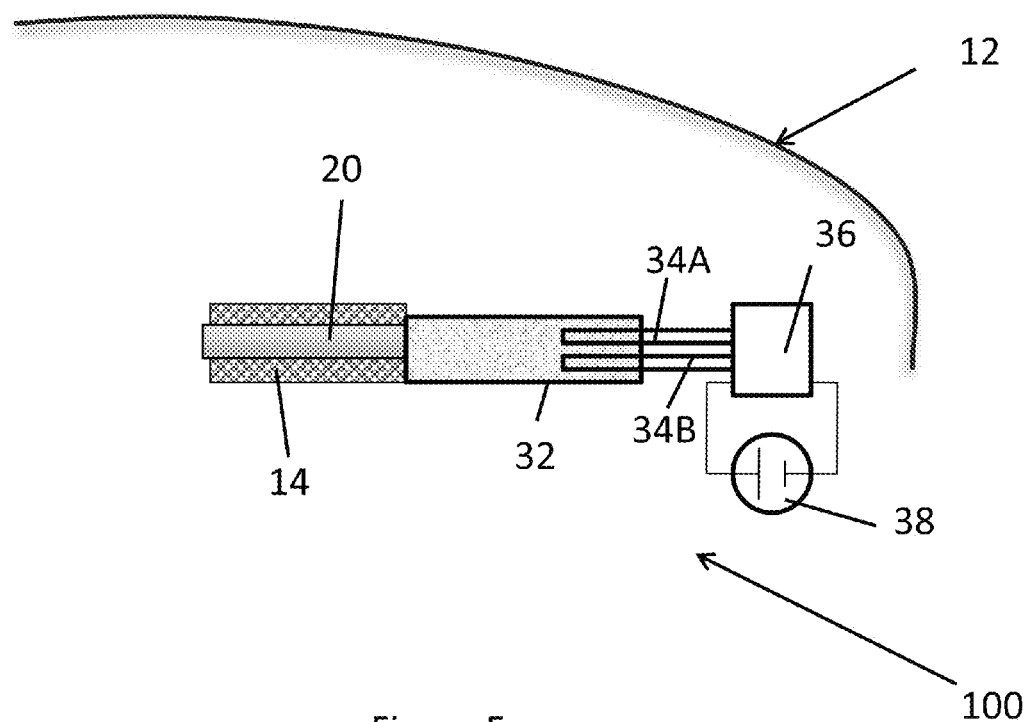

FIG. 5 schematically depicts a medical system according to another exemplary embodiment of the current invention.

Figure 6:
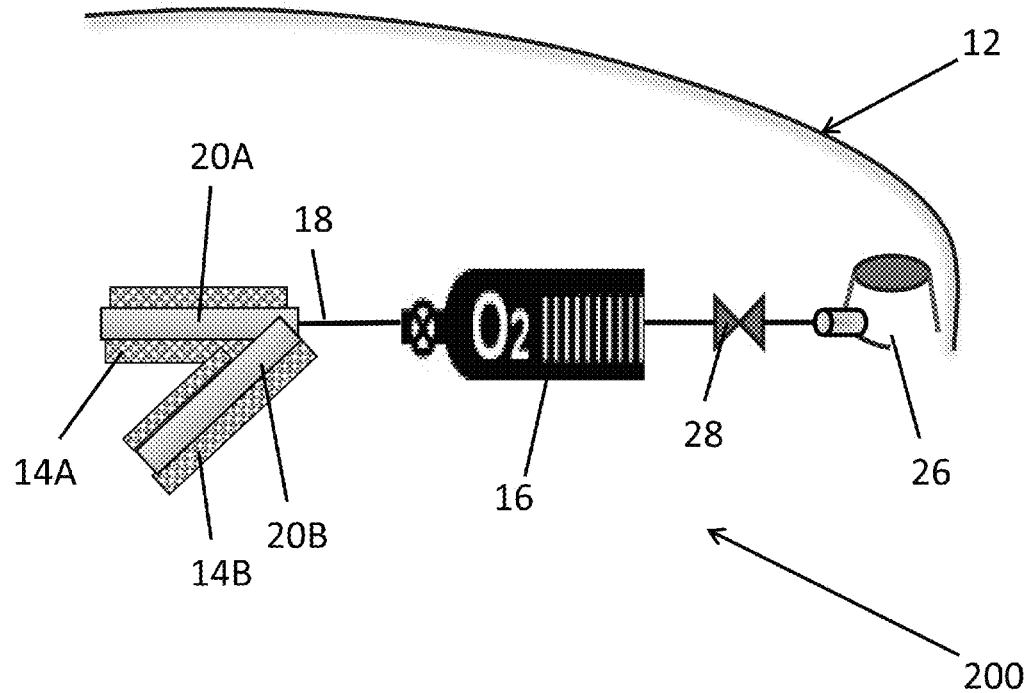

FIG. 6 illustrates a medical system according to yet another exemplary embodiment provided with a plurality of functional cells unit.

Figure 7A:
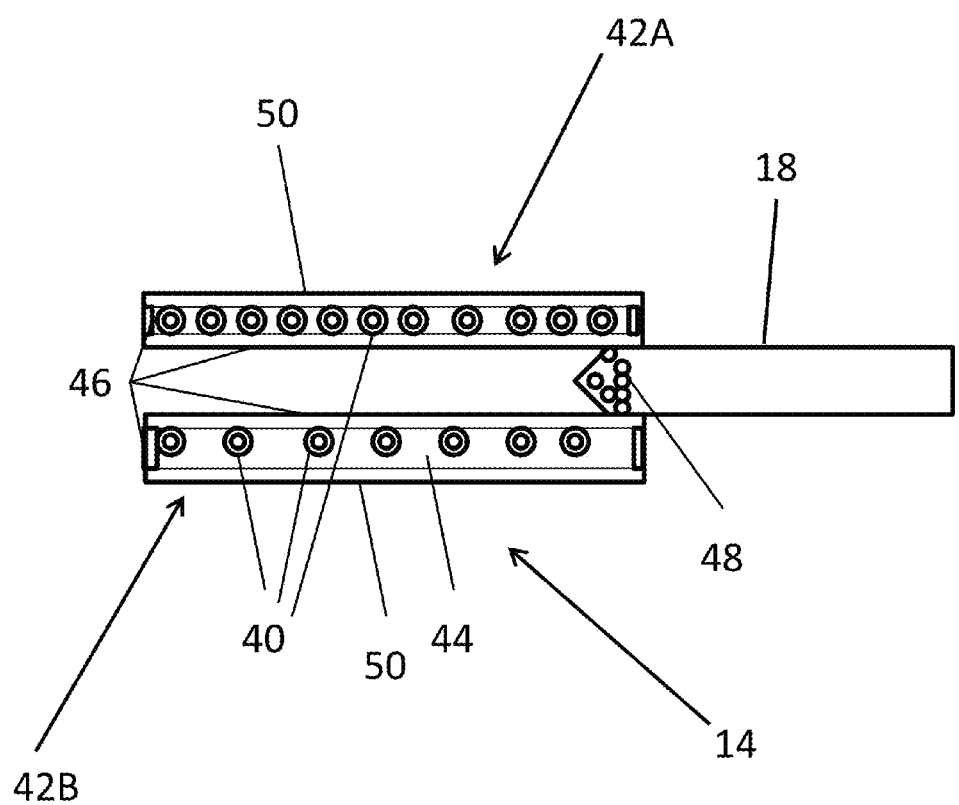

FIG. 7a illustrates a functional cell unit according to a preferred embodiment.

Figure 7B:
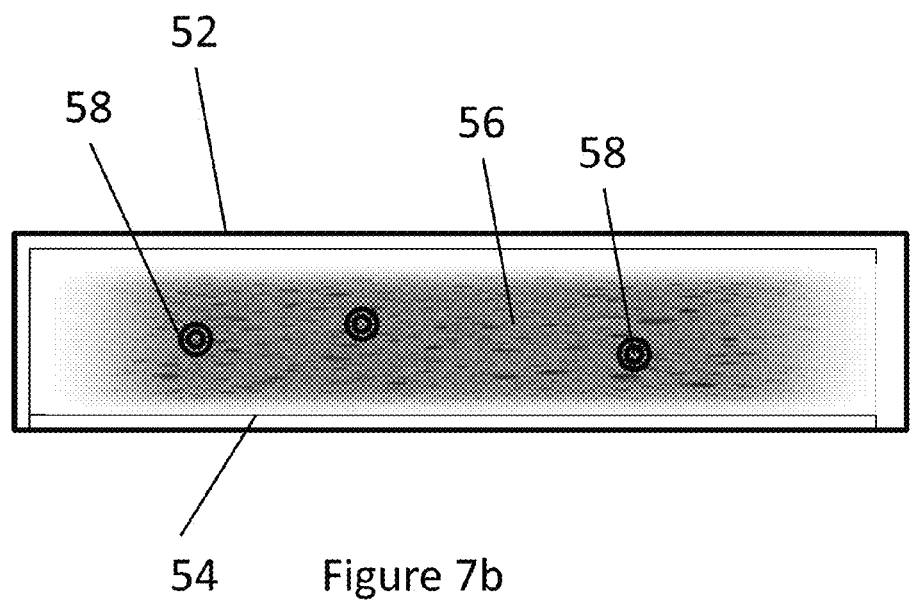

FIG. 7b illustrates a compartment of a functional cell unit according to another preferred embodiment.

Figure 7C:
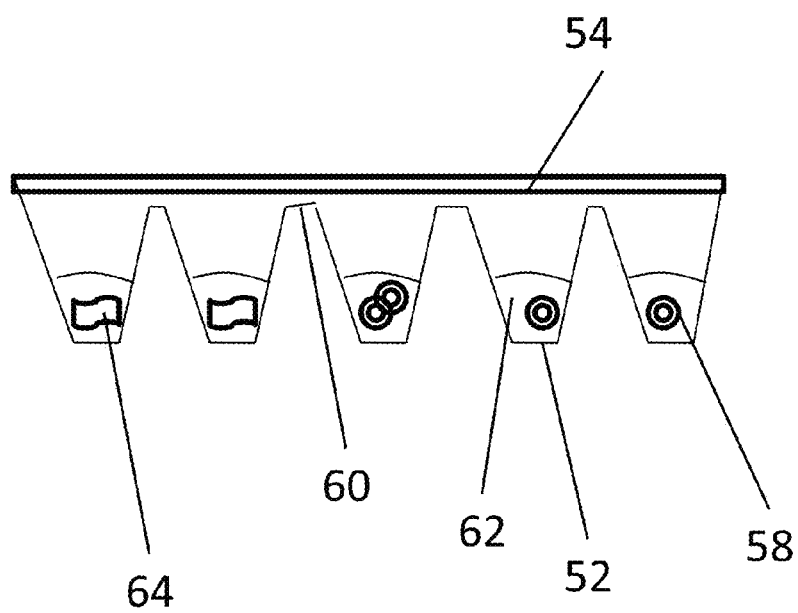

FIG. 7c illustrates a compartment of a functional cell unit according to yet another preferred embodiment.

Figure 7D:
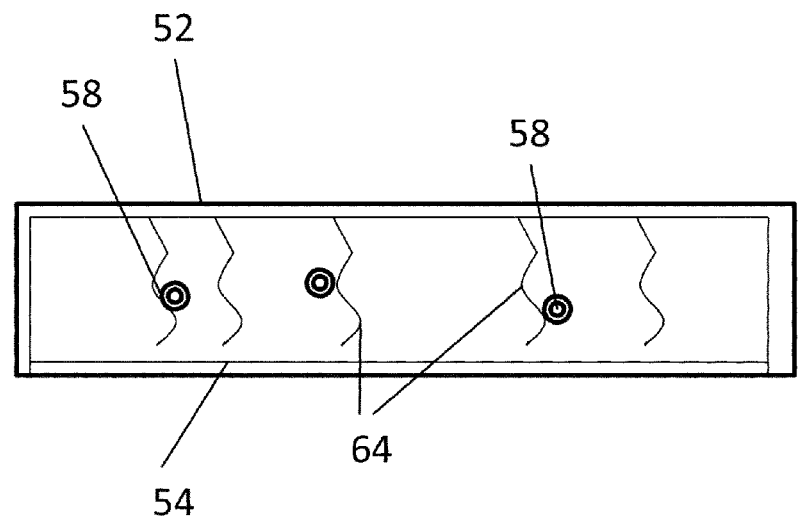

FIG. 7d illustrates a compartment of a functional cell unit according to yet another preferred embodiment.

Figure 8:
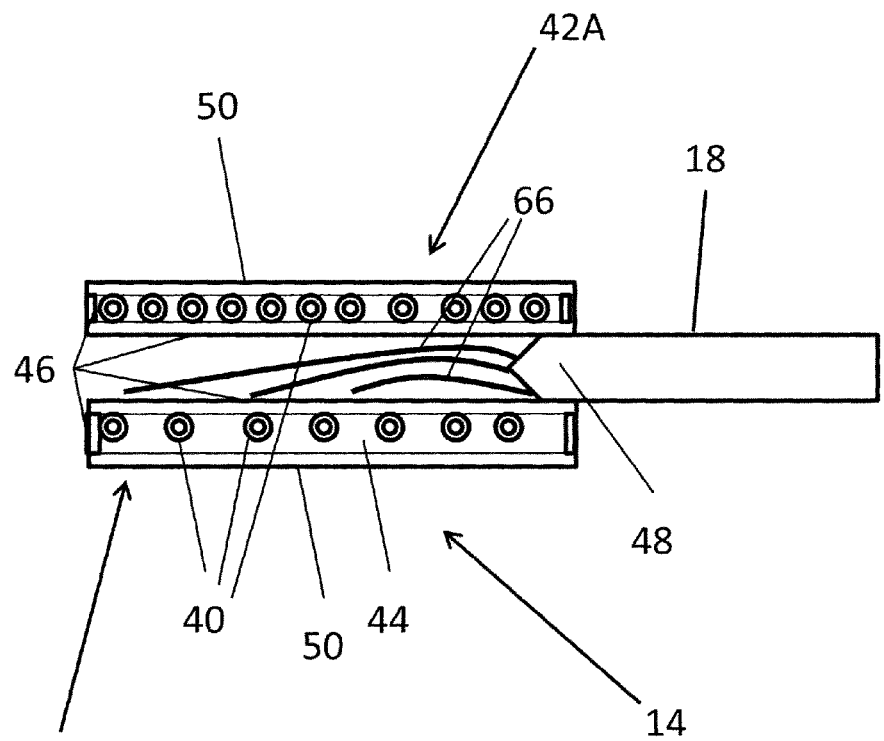

FIG. 8 illustrates an oxygen distributor according to another preferred embodiment.

DESCRIPTION OF THE PREFERRED EMBODIMENTS

The present invention relates generally to an implantable medical devices without immunosuppressive therapy and to an apparatus and method in which oxygen is in constant availability to the transplanted cells, e.g., cells in transplanted pancreatic islets within the implanted medical device.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts.

The drawings are generally not to scale. Some optional parts were drawn using dashed lines.

For clarity, non-essential elements were omitted from some of the drawings.

FIG. 1 schematically depicts a medical system 20 according to an exemplary embodiment.

Medical system 10 is subcutaneously implanted beneath the skin 12 of a patient, relatively close to the skin. Medical system 10 comprises a unit 14 that accommodate the functional cells or functional tissue. Functional cells can be selected from a group of cells such as islets of Langerhans, adrenal cells, stem cells and genetic implantable cells. The functional cell unit 14 is configured in a coin-like shape that maintains the unit flexible enough so as to be able to adjust to the movements of the body and encounter minimal discomfort to the patient.

The physical flexibility of the unit is such that the unit follows partially the natural movements of the body organs that are adjacent to it. As an example, if the unit is adjacent to a muscle tissue, when the tissue is stretched, the unit should accommodate itself in partial or in full to the stretching movement. Moreover, one possible location for transplants of such devices is beneath the skin in the abdomen area and this area is susceptible to be leaned on, the unit should have the flexibility to adjust itself to the item that leans on it such as a table, when a person is sitting.

Preferable dimensions of a disc-like shaped unit 14 are 1-8 mm in thickness and a diameter of about 1-20 cm. It should be noted that any other shape can be utilized as long as one of the dimensions of the unit is small relative to the others, rendering the desired flexibility to the unit.

The implanted medical system 10 further comprises a gas unit 16. The gas unit 16 is preferably a pressurized reservoir that can be implanted within the body wherein the reservoir can also be flexible, but can also be stiff. Usually, it is preferable that the gas content will be about 95% oxygen and 5% carbon dioxide, in any case, the gas comprises essentially oxygen. The pressure range should be more than one atmosphere (the environment pressure) and up to 100 atmospheres; however, the preferable range is between 1-10 atmospheres.

The gas unit 16 and the distributor 20 are fluidically connected through a gas tube 18. Gas (essentially oxygen) is transferred through tube 18 from the gas unit to supply oxygen to the cells unit so as to maintain the cells in viable condition. The pressure in the tube 18 shouldn't exceed about 1-3 atmospheres, where 1 atm is the ambient pressure. The gas can be released into the functional cells unit 14 through an oxygen distributor 20. From the oxygen distributor, the gas diffuses to the functional cells as will be explained herein after.

The release of the gas from the gas unit 16 can be performed using different methods. One option is to install an electrical valve or electrical gate. Another option is the use of special mechanical valve.

The gas within the gas unit 16 can be replenished through a gas replenishing port 26. The port should be positioned in the vicinity of the skin 12. A one-direction valve 28 is positioned between the port 26 and the gas unit 16 so as to ensure that all the gas being accumulated within the gas unit 16 and a pressure above one atmosphere is maintained within the gas unit. The gas can replenish by inserting a needle through the skin 12 of the patient and into the port 26 through a membrane, typically silicon-rubber that is provided in the port and placed adjacent the skin.

Reference is now made to FIG. 2a illustrates a system for controlled flow of gas incorporated in the system shown in FIG. 1. The electrical valve can be a gas solenoid valve 22 made of parts that receive electrical impulses and then translate those impulses into mechanical movements that opens or closes the valve and controls the flow of gas to the cells unit. Optionally, the gas solenoid valve's housing is provided with a coil that sits inside and receives the electrical currents from at least one sensor 24 that may be positioned in the oxygen distributor 20 or in the vicinity of the functional cells. The sensor 24 senses the amount of oxygen in the distributor 20, as shown in FIG. 2 and operates the electric valve 22. When the level of oxygen in the distributor 20 reaches a predetermined threshold (e.g. 300 mm Hg), the sensor 24 sends an electrical signal to valve 22. The solenoid valve 22 then converts the electrical impulses received by the coil into mechanical parts inside the valve to open the valve and release an additional amount of gas. This is repeated. The gas in the tank is dropping in steps while after a while and when the gas level approaches about one atmosphere, the ambient pressure; the gas in the gas unit 16 should be replenished.

Optionally, the pressure control can be performed by mechanical means in which a spring or pressure differences controls the transfer of gas from the gas unit 16 to the tube 18.

Optionally, a membrane can be placed between the gas unit 16 and the tube 18. In this case, a relatively continuous and steady flow of gas to the functional cells in the cells unit 14 can be accomplished.

Optionally, pressure control can be performed by electrical gate opened in predetermined time intervals based, as an example, on the expected consumption of oxygen.

Optionally, the valve can be a mechanical valve that is operated based on pressure differences between the gas unit 16 and the distributor 20.

Reference is now made to FIG. 3 illustrating the port when replenished with gas from outside the body in accordance with one embodiment. A needle 30c is inserted through the skin 12 and into the port 26 through a membrane 30 (e.g. silicon rubber membrane) that is being punctured by the needle 30c. The needle is connected to a tube 29c from which the gas is inserted in the needed pressure.

Optionally, the port 26 is incorporated within the gas unit 16, as shown in FIG. 4.

All components of the implanted medical system are made of materials that are biocompatible and are adapted to be accommodated within the body of a patient for a relatively long period of time (e.g. years).

Alternatively, an oxygen generator can be employed in order to prevent the need to puncture the skin each time replenishment of gas is needed. The oxygen generator may be located separately from the functional cells unit 14, or instead of the distributor 20. Reference is now made to FIG. 5 schematically depicting a medical system according to another exemplary embodiment of the current invention. System 100 comprises the functional cells unit 14 and an oxygen distributor 20 that receives oxygen from a chamber 32 that constantly delivers oxygen to the functional cells unit 14 so as to assure the cells are viable. The oxygen generator comprises pair of electrodes 34A and 34B that are preferably flexible and are positioned partially within the chamber 32. The electrodes are preferably made of a biocompatible material such as carbon or platinum. The system further comprises a power source 38 and a microprocessor 36. When an electrical potential is generated between the electrodes 34A and 34B by the power source 38, hydrolysis of water molecules is initiated and resulted in oxygen production. The oxygen generated in 32 is diffused to the distributor 20 and to the functional cells unit.

It is optional to provide an oxygen sensor (not shown in the figures) that detects the oxygen level and accordingly initiate or stop the current between the electrodes using the microprocessor 36. The amount of oxygen generation is controllable in this way.

The amount of functional cells needed depends on physiological characteristics of the patient as well as the condition of the disease. Optionally, the gas unit is connected to several cell units as shown in FIG. 6, illustrating a medical system according to yet another exemplary embodiment provided with a plurality of functional cells unit. Medical System 200 comprises the same elements as in FIG. 1, however, more than one distributer 20A and 20B as well as more than one functional cells Unit 14A and 14B are provided. More cells units with their own distributor of oxygen or a shared one can be employed in the system.

As mentioned herein before, the functional cell unit 14 is preferably shaped as a disc-like member that has some degree of flexibility. Preferably, there are two adjacent compartments wherein the gas is distributed between them.

Reference is now made to FIG. 7a illustrating a functional cell unit 14 according to a preferred embodiment into which the distributor 20 is distributing the gas. The gas can be distributed directly from a nozzle of the tube or through plurality holes 48, as an example. In the disclosed preferred embodiment, functional cells 40 are being preferably embedded within a matrix 44 in two disc shaped compartments 42A and 42B facing each other on both sides of the distributor 18. It should be noted that the cells can be also a tissue, like islets of Langerhans. The matrix in which the cells are embedded can be selected from a group of materials such as alginate, collagen, a combination thereof, or any other material in which oxygen as well as nutrients can diffuse within.

Each face of the disc-like compartment that faces the opposite compartment as well as the sides of the compartments are covered by a layer of preferably silicone or hydrolyzed silicone 46 that allows oxygen to pass through and get into the matrix in which the functional cells are embedded. The opposite face of the disc-like compartment (outer sides) is covered with a layer 50 that is permeable to nutrients such as glucose, but is impermeable to immunologic factors that might attack the cells like immune cells and immune globuloins (e.g. IgG). Layer 50 can be made of materials such as alginate or PEG or combination with other materials such as Teflon.

Such compartment should be in a thickness that is low enough to prevent aggregation of the cells. In the case of Langerhans Islets, the thickness of the disc-like structure should be about between 200 and 2,000 µm. If single cells are being utilized, the thickness of the unit can be about 20 µm.

It is important to keep the surface area through which the oxygen passes to the cells as large as possible in order to ensure the viability of the cells.

Reference is now made to FIG. 7b illustrating for clarity, another compartment of the functional cells unit. As in the former embodiment, the faces that are exposed to the distributor of gas or oxygen from a generator are covered with silicone layer 52 that allows the passage of oxygen gas through the layer into the cell compartment. The opposite face is covered with a layer 58 that is allowing nutrients to get into the compartment. Within the compartment, a sponge-like material having a porous structure 56 is received onto which the functional cells 58 are immobilized or captured. The porous structure 56 should have pores that are sized so as to allow the functional cells to get inside and be entrapped within the pores.

Reference is now made to FIG. 7c illustrating for clarity, another embodiment of a compartment of the functional cells unit. As in the former embodiments, the faces that are exposed to the distributor of gas or oxygen from a generator are covered with silicone layer 52 that allows the passage of oxygen through the layer into the compartment. The opposite face is covered with a layer 58 that is allowing nutrients to get into the compartment and allowing the hormone or other bio-materials that are produced by the functional cells, to diffuse outside. The compartment itself is built from a plurality of subunits built in a shape that could be similar to an egg carton. This structure is preferable from the following reasons: the surface area that is occupied in allowing the oxygen to pass through and reach the cells is relatively large and the thin areas 60 between the subunits render flexibility to the whole structure. Within each subunit, it is provided functional cells 58 or tissues 64 embedded within a matrix 62 such as alginate, collagen or a combination therein. In the preparation of the functional cells unit, liquid or semi-liquid alginate, as an example, can be mixed with the functional cells and poured to within the subunits so as to fill it. Another option is to accommodate a mass of matrix mixed with the functional cells in a certain shape within each subunit.

The typical diameter of each subunit can be in the range of 10-2,500 µm.

Reference is now made to FIG. 7d illustrating for clarity reasons, yet another compartment of the functional cells unit. As in the former embodiments, the faces that are exposed to the distributor of gas or oxygen from a generator are covered with silicone layer 52 that allows the passage of oxygen through the layer into the compartment. The opposite face is covered with a layer 58 that is allowing nutrients to get into the compartment and allowing the hormone to get out of the compartment. Within the compartment, hair-like structures or inner projections 64 are provided onto which the functional cells 58 are captured and the structure is strengthen. It is preferable that the projections 64 will be made from materials such as silicone so as to facilitate the transfer of oxygen to the functional cells.

Reference is now made to FIG. 8 illustrating a distributor according to another preferred embodiment. In order to uniformly transfer the oxygen to the functional cells that are embedded within a the structures as illustrated in FIGS. 7a-7d, the distributor of gas or oxygen can be provided with means to better distribute the gas to the cells. This is an important feature of the present invention. The functional unit shown in FIG. 8 is the embodiment shown in FIG. 7a, however, this distribution of gas can be employed in any other embodiment that is shown as well as others. Distributor 18 is provided with plurality of small tubes 66, each have a nozzle in a different area of the functional cell unit 14. In this way, the availability of oxygen is similar for the cells in any of the areas of the cells unit, whether they are close to the distributor or far from it.

It should be noted that the outer layer of the functional cells unit and other parts of the system contains materials that promote vascularization in the vicinity of the implanted system as well as other materials that should increase the immunedepression reaction of the body of the patient. For the purpose of inducing a dense vascular bed close to the active surfaces of the functional cells unit, it is optional to add bioactive agents such as Heparin, CSPG, HSPG, platelets derivatives, and mesenchymal stem cells. Reducing the local inflammation can be performed by adding materials such as alpha-1 anti-trypsin, Anti-TNF-a (e.g. etanercept/Enbrel, pentoxifylline), and hMSC.

Each part of the system and the system as a whole can be manufactured by using a 3D printer while keeping the material bio-compatible.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An implantable medical system comprising:
a replenishment port configured to be implanted subcutaneously and configured to receive gas through a needle adapted to penetrate the replenishment port through skin;
a subcutaneous gas unit configured to be implanted subcutaneously at a different location from the replenishment port, the gas unit comprising a pressurized reservoir configured to be replenished by the gas received into the replenishment port, wherein the gas unit is configured to maintain a pressure within the pressurized reservoir that is greater than one atmosphere, wherein the gas comprises oxygen;
at least one functional cells unit configured to be implanted subcutaneously at a different location from the replenishment port and the subcutaneous gas unit, the at least one functional cells unit containing a plurality of functional cells and configured to receive oxygen from the subcutaneous gas unit so as to maintain the functional cells in a viable condition; and
a subcutaneous unidirectional valve positioned between the pressurized reservoir of the subcutaneous gas unit and the at least one functional cells unit, wherein the valve is configured to regulate flow of the gas from the subcutaneous gas unit to the at least one functional cells unit.

2. The implantable medical system as claimed in claim 1, further comprising at least one distributor configured to distribute the gas from the subcutaneous gas unit to the at least one functional cells unit.

3. The implantable medical system as claimed in claim 1, wherein a unidirectional valve is provided between the replenishment port and the pressurized reservoir to ensure gas is solely transferred from the replenishment port to the pressurized reservoir.

4. The implantable medical system as claimed in claim 1, wherein the functional cells are selected from a group comprising islets of Langerhans, adrenal cells, stem cells and genetic implantable cells.

5. The implantable medical system as claimed in claim 1, wherein the at least one functional cells unit has one dimension that is relatively longer than other dimensions so as to render flexibility to the unit, and wherein the at least one functional cells unit is flexible enough so as to allow the at least one functional cells unit to partially follow the natural movements of the body organs that are adjacent to the at least one functional cells unit.

6. The implantable medical system as claimed in claim 1, wherein the at least one functional cells unit is in a shape of a disc having a thickness of 1-8 mm and a diameter of 1-20 cm.

7. The implantable medical system as claimed in claim 1, wherein the at least one functional cells unit comprises opposite positioned compartments of substantially the same dimensions, both compartments are configured to allow the diffusion of oxygen to the functional cells inside the at least one functional cells unit.

8. The implantable medical system as claimed in claim 7, wherein the at least one functional cells unit is covered with a layer that facilitates transfer of oxygen.

9. The implantable medical system as claimed in claim 8, wherein the layer is a silicone layer.

10. The implantable medical system as claimed in claim 1, wherein outer sides of the at least one functional cells unit is covered with a layer permeable to nutrients and biomaterials that may be produced by the functional cells and impermeable to immunologic factors and oxygen.

11. The implantable medical system as claimed in claim 7, wherein the compartments are disc-like and are have a thickness of about 20-2,000 μm.

12. The implantable medical system as claimed in claim 1, wherein the functional cells are embedded in a matrix within the at least one functional cells unit.

13. The implantable medical system as claimed in claim 1, wherein the matrix is made of materials selected from a group that comprises alginate, collagen, and combination thereof.

14. The implantable medical system as claimed in claim 1, wherein the functional cells in the at least one functional cells unit are trapped within a porous structure.

15. The implantable medical system as claimed in claim 1, wherein the at least one functional cells unit comprises a plurality of subunits provided with functional cells embedded in a matrix, wherein the plurality of subunits are configured to allow the diffusion of oxygen to the functional cells.

16. The implantable medical system as claimed in claim 15, wherein the diameter of each subunit is about 10-2,500 µm.

17. The implantable medical system as claimed in claim 1, wherein the at least one functional cells unit is provided with inner projections configured to allow the functional cells to be captured thereby.

\* \* \* \* \*